United States Patent [19]

Nanjo et al.

[11] Patent Number: 5,405,961
[45] Date of Patent: Apr. 11, 1995

[54] ORGANOPHOSPHORUS COMPOUNDS AND INSECTICIDAL, ACARICIDAL AND NEMATOCIDAL COMPOSITIONS CONTAINING SAME

[75] Inventors: Katsumi Nanjo, Tokorozawa; Akinori Kariya; Shinya Henmi, both of Higashi-Murayama, all of Japan

[73] Assignee: Agro-Kanesho Co., Ltd., Tokyo, Japan

[21] Appl. No.: 104,909

[22] Filed: Aug. 12, 1993

Related U.S. Application Data

[62] Division of Ser. No. 726,211, Jul. 5, 1991, Pat. No. 5,280,123.

[30] Foreign Application Priority Data

Jul. 6, 1990 [JP] Japan .................. 2-178825
Apr. 8, 1991 [JP] Japan .................. 3-75327

[51] Int. Cl.$^6$ .......... C07F 9/02; C07F 9/28; A01N 57/00; A01N 43/50
[52] U.S. Cl. .................. 544/243; 504/127; 504/128; 548/111
[58] Field of Search .......... 544/243; 548/111; 514/94, 398, 401; 504/127, 128

[56] References Cited

U.S. PATENT DOCUMENTS

| | | | |
|---|---|---|---|
| 4,590,182 | 5/1986 | Haga et al. | 514/80 |
| 4,607,031 | 8/1986 | Yoshino et al. | 514/211 |
| 4,645,761 | 2/1987 | Haga et al. | 514/94 |
| 4,720,488 | 1/1988 | Hayase et al. | 514/92 |
| 4,839,349 | 6/1989 | Covey et al. | 514/92 |
| 5,264,426 | 11/1993 | Sommer et al. | 514/94 |
| 5,280,123 | 12/1993 | Nanjo et al. | 548/111 |

FOREIGN PATENT DOCUMENTS

| | | | |
|---|---|---|---|
| 0464830 | 1/1992 | European Pat. Off. | 548/111 |
| 0403376 | 6/1966 | Switzerland | 548/111 |
| 1768607 | 10/1992 | U.S.S.R. | 544/243 |

*Primary Examiner*—Floyd D. Higel
*Attorney, Agent, or Firm*—Oblon, Spivak, McClelland, Maier & Neustadt

[57] ABSTRACT

Insecticidal, acaricidal or nematocidal compositions which comprise a series of organophosphorus compounds represented by the compounds represented by the following structural formulae:

$$H_3CN-N\underset{\underset{NCN}{\|}}{\diagdown}N-\underset{\underset{}{\|}}{\overset{O}{P}}\diagup\overset{OC_2H_5}{\diagdown}S\text{-}n\text{-}C_3H_7$$

and $$CH_3OCH_2-N\underset{\underset{NCN}{\|}}{\diagdown}N-\underset{\underset{}{\|}}{\overset{O}{P}}\diagup\overset{OC_2H_5}{\diagdown}S\text{-}sec\text{-}C_4H_9$$

show excellent effect for controlling harmful insects, mites and nematodes, do not give off a bad or irritating odor and exhibit very low toxicity to warm-blooded animals.

6 Claims, No Drawings

ORGANOPHOSPHORUS COMPOUNDS AND INSECTICIDAL, ACARICIDAL AND NEMATOCIDAL COMPOSITIONS CONTAINING SAME

This is a division of application Ser. No. 07/726,211, filed on Jul. 5, 1991, now U.S. Pat. No. 5,280,123.

BACKGROUND OF THE INVENTION (Field of the Invention) The present invention relates to an organophosphorus compound represented by the following general formula (I):

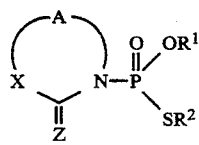

[wherein $R^1$ and $R^2$ each represents a $C_1$ to $C_4$ alkyl group; X represents O, S, $CH_2$, CH—$R^3$ (wherein $R^3$ represents a $C_1$ to $C_3$ alkyl group), NH or N—$R^4$ {wherein $R^4$ represents a $C_1$ to $C_4$ alkyl group (the alkyl group may be substituted with at least one group selected from the group consisting of alkoxy, alkylthio, cyano, alkoxyalkyloxy and alkylamino groups and halogen atoms), an alkenyl group which may be substituted with halogen atoms, an alkynyl group which may be substituted with halogen atoms, a phosphoric acid ester radical, a cyano group, a group of the following general formula (II):

(wherein $R^3$ represents an alkyl or alkylamino group which may be substituted with halogen atoms) or a group represented by the following general formula: —($R^6$)$_n$—CO—$R^7$ (wherein n is 0 or 1; $R^6$ represents a methylene group which may be substituted with alkyl groups, or an ethylene group which may be substituted with alkyl groups; $R^7$ represents an alkyl group which may be substituted with halogen atoms, an alkoxy group which may be substituted with halogen atoms, an alkylthio group, an alkylamino group or a hydrogen atom}; Z represents a group represented by the general formula: N—$R^8$ ($R^8$ represents a nitro group, a cyano group, an alkylsulfonyl group which may be substituted with halogen atoms, a tosyl group or an alkylcarbonyl group which may be substituted with halogen atoms) or a group represented by the general formula: C(CN)$R^9$ (wherein $R^9$ represents a cyano group or an alkoxycarbonyl group); and A represents an ethylene group which may be substituted with $C_1$ to $C_3$ alkyl groups, a trimethylene group which may be substituted with $C_1$ to $C_3$ alkyl groups or a group represented by the general formula: —$CH_2NR^{10}CH_2$— (wherein $R^{10}$ is a $C_1$ to $C_3$ alkyl group)]. The compound of formula (I) according to the present invention specifically excludes an organophosphorus compound of the general formula (I) in which $R^1$ and $R^2$ are $C_1$ to $C_4$ alkyl groups respectively, X is NH, Z is a cyanoimino group or a nitroimino group and A is an ethylene group which may be substituted with $C_1$ to $C_3$ alkyl groups or a trimethylene group which may be substituted with $C_1$ to $C_3$ alkyl groups.

The present invention also relates to a method for preparing the compound, of formula (I), and insecticides, acaricides and nematocides which comprise the compound as an active ingredient.

(Prior Art Statement)

Recently, organophosphorus compounds having an imidazolidinyl group have been investigated and developed. For instance, Japanese Unexamined Patent Publication No. She 61-267594 and Japanese Unexamined Patent Publication No. Hei 2-793 disclose that these compounds can be used as insecticides, acaricides, nematocides and agents for killing soil insect pests. However, these patents simply disclose organophosphorus compounds having an imidazolidine skeleton which carries an oxygen or sulfur atom on the 2-position. Moreover, the insecticidal, acaricidal and nematocidal effects of these compounds are insufficient and are not necessarily satisfactory.

OBJECTS AND SUMMARY OF THE INVENTION

Accordingly, an object of the present invention is to provide a novel organophosphorus compound represented by the foregoing general formula (I).

Another object of the present invention is to provide a method for preparing a novel organophosphorus compound represented by the foregoing general formula (I).

A further object of the present invention is to provide an agricultural chemical having insecticidal, acaricidal and nematocidal effects higher than those attained by conventional agricultural chemicals and exhibiting very low toxicity to warm-blooded animals.

The inventors of this invention have synthesized a variety of organophosphorus compounds carrying an imidazolidinyl group and have investigated the insecticidal, acaricidal and nematocidal activities of the organophosphorus compounds having an imidazolidine skeleton which carries a specific substituent on the 2-position in order to develop effective insecticides, acaricides and nematocides. As a result, the inventors have found out that excellent control of harmful insect pests can be achieved by an organophosphorus compound (hereinafter referred to as "the compound of the present invention") represented by the following general formula (I):

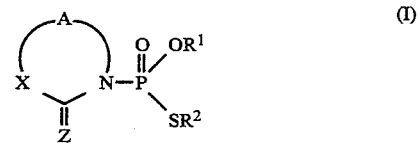

[wherein $R^1$ and $R^2$ each represents a $C_1$ to $C_4$ alkyl group; X represents O, S, $CH_2$, CH—$R^3$ (wherein $R^3$ represents a $C_1$ to $C_3$ alkyl group), NH or N—$R^4$ {wherein $R^4$ represents a $C_1$ to $C_4$ alkyl group (the alkyl group may be substituted with at least one group selected from the group consisting of alkoxy, alkylthio, cyano, alkoxyalkyloxy and alkylamino groups and halogen atoms), an alkenyl group which may be substituted with halogen atoms, an alkynyl group which may be substituted with halogen atoms, a phosphoric acid ester radical, a cyano group, a group of the following general formula (II):

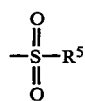
(II)

(wherein $R^3$ represents an alkyl or alkylamino group which may be substituted with halogen atoms) or a group represented by the following general formula: $—(R^5)_n—CO—R^7$ (wherein n is 0 or 1; $R^6$ represents a methylene group which may be substituted with alkyl groups, or an ethylene group which may be substituted with alkyl groups; $R^7$ represents an alkyl group which may be substituted with halogen atoms, an alkoxy group which may be substituted with halogen atoms, an alkylthio group, an alkylamino group or a hydrogen atom)}; Z represents a group represented by the general formula: $N—R^8$ ($R^8$ represents a nitro group, a cyano group, an alkylsulfonyl group which may be substituted with halogen atoms, a tosyl group or an alkylcarbonyl group which may be substituted with halogen atoms) or a group represented by the general formula: $C(CN)R^9$ (wherein $R^9$ represents a cyano group or an alkoxycarbonyl group); and A represents an ethylene group which may be substituted with $C_1$ to $C_3$ alkyl groups, a trimethylene group which may be substituted with $C_1$ to $C_3$ alkyl groups or a group represented by the general formula: $—CH_2NR^{10}CH_2—$ (wherein $R^{10}$ is a $C_1$ to $C_3$ alkyl group)]. The compound of formula (I) according to the present invention specifically excludes an organophosphorus compound of the general formula (I) in which $R^1$ and $R^2$ are $C_1$ to $C_4$ alkyl groups respectively, X is NH, Z is a cyanoimino group or a nitroimino group and A is an ethylene group which may be substituted with $C_1$ to $C_3$ alkyl groups or a trimethylene group which may be substituted with $C_1$ to $C_3$ alkyl groups. Thus, the present invention has completed on the basis of the foregoing finding.

These organophosphorus compounds do not give off any bad or irritating odor and have low toxicity to warm-blooded animals. Therefore, they can widely be used and thus have very high usefulness.

The organophosphorus compounds represented by the foregoing general formula (I) also include stereoisomers such as optical isomers. In addition, in the general formula (I), when X is the group NH, the organophosphorus compounds may exist in the form of a tautomer represented by the following general formula (I'):

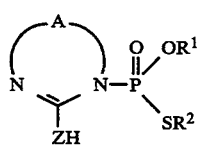
(I')

(wherein $R^1$, $R^2$, Z and A are the same as those defined above). These compounds (tautomeric isomers) are likewise included in the scope of the compound of the present invention.

DETAILED DESCRIPTION OF THE PREFERRED EMBODIMENTS

The compounds of the present invention can be prepared in accordance with, for instance, any one of the following three methods.

Method (i)

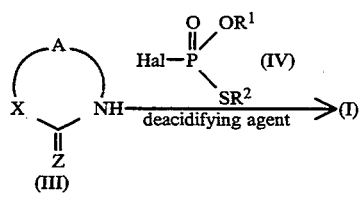

Method (ii) (in the formula (I), X is a group: $NR^4$)

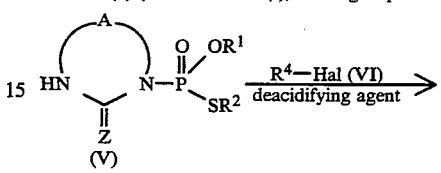

Method (iii)

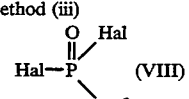

(Wherein $R^1$, $R^2$, $R^4$, X, Z and A are the same as those defined above and Hal means a halogen atom).

The foregoing reactions are in general carried out at a temperature ranging from $-100°$ to $+60°$ C. and preferably from $-80°$ to $30°$ C. Moreover, these reactions are performed in the presence of a deacidifying agent, examples of which include organic lithium compounds such as n-butyl lithium, t-butyl lithium and phenyl lithium; inorganic bases such as sodium hydride, potassium hydride, metallic sodium, sodium hydroxide and potassium hydroxide; alkoxides such as sodium methoxide, sodium ethoxide and potassium t-butoxide; and organic bases such as triethylamine and pyridine.

In addition, these reactions are desirably carried out in the presence of a solvent. Examples of such solvents include aromatic hydrocarbons such as benzene, toluene, xylene and chlorobenzene; cyclic or non-cyclic aliphatic hydrocarbons such as hexane and cyclohexane; ethers such as diethyl ether, methyl ethyl ether, dioxane and tetrahydrofuran; nitriles such as acetonitrile, propionitrile and acrylonitrile; and aprotic polar solvents such as dimethylformamide, dimethylsulfoxide, sulfolane and hexamethyl-phosphoric acid triamide.

Typical examples of the compounds of the present invention will now be listed in the following Table 1. Each compound will hereinafter be described by the corresponding number of the compound.

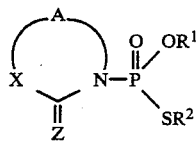

(I)

In the following Table 1, the symbol "←" as set forth in the column, "←A—" represents a bond with X and "ph" means a p-phenylene group.

TABLE 1

| Comp. No. | R¹ | R² | ←A— | X | Z | Physical Property |
|---|---|---|---|---|---|---|
| 1 | C₂H₅ | n-C₃H₇ | —(CH₂)₂— | N—CH₃ | N—NO₂ | m.p.: 46.0~48.0° C. |
| 2 | C₂H₅ | n-C₃H₇ | —(CH₂)₂— | N—C₂H₅ | N—NO₂ | oily substance |
| 3 | C₂H₅ | n-C₃H₇ | —(CH₂)₂— | N—CH₃ | N—CN | oily substance |
| 4 | C₂H₅ | n-C₃H₇ | —(CH₂)₂— | N—C₂H₅ | N—CN | oily substance |
| 5 | C₂H₅ | n-C₃H₇ | —(CH₂)₂— | N-n-C₃H₇ | N—CN | oily substance |
| 6 | C₂H₅ | n-C₃H₇ | —(CH₂)₂— | N-n-C₄H₉ | N—CN | oily substance |
| 7 | C₂H₅ | n-C₃H₇ | —(CH₂)₂— | NH | C(CN)₂ | oily substance |
| 8 | C₂H₅ | n-C₃H₇ | —(CH₂)₂— | NH | N—SO₂-ph-4-CH₃ | oily substance |
| 9 | C₂H₅ | n-C₃H₇ | —(CH₂)₂—NH | N—SO₂CH₃ |  | oily substance |
| 10 | C₂H₅ | n-C₃H₇ | —(CH₂)₂— | S | N—SO₂CH₃ | oily substance |
| 11 | C₂H₅ | n-C₃H₇ | —(CH₂)₂— | S | N—CN | oily substance |
| 12 | C₂H₅ | n-C₃H₇ | —(CH₂)₂— | S | N—NO₂ | oily substance |
| 13 | C₂H₅ | sec-C₄H₉ | —(CH₂)₃— | N—CH₃ | C—CN | oily substance |
| 14 | C₂H₅ | n-C₃H₇ | —(CH₂)₂— | N—P(O)(OC₂H₅)—S-n-C₃H₇ | N—CN | oily substance |
| 15 | C₂H₅ | sec-C₄H₉ | —(CH₂)₂— | N—CH(CH₃)₂ | N—CN | oily substance |
| 16 | C₂H₅ | sec-C₄H₉ | —(CH₂)₂— | N—CH₃ | N—CN | m.p.: 45.0~47.0° C. |
| 17 | C₂H₅ | n-C₃H₇ | —(CH₂)₃— | N—CH₃ | C(CN)₂ | oily substance |
| 18 | C₂H₅ | n-C₃H₇ | —(CH₂)₂— | N—CH₃ | C(CN)₂ | oily substance |
| 19 | C₂H₅ | n-C₃H₇ | —(CH₂)₂— | N—CH₃ | N—SO₂CH₃ | oily substance |
| 20 | C₂H₅ | sec-C₄H₉ | —(CH₂)₂— | N—CH₃ | C(CN)₂ | m.p.: 73.0~76.0° C. |
| 21 | C₂H₅ | n-C₃H₇ | —CH₂NCH₂— CH₃ | NH | N—NO₂ | oily substance |
| 22 | C₂H₅ | n-C₃H₇ | " | N—CH₃ | N—NO₂ | oily substance |
| 23 | C₂H₅ | n-C₃H₇ | " | N-n-C₃H₇ | N—NO₂ | oily substance |
| 24 | C₂H₅ | n-C₃H₇ | —(CH₂)₂— | N—CH₂CH=CH₂ | N—NO₂ | oily substance |
| 25 | C₂H₅ | n-C₃H₇ | —(CH₂)₂— | N—CH₃ | N—SO₂CF₃ | oily substance |
| 26 | C₂H₅ | n-C₃H₇ | —(CH₂)₂— | N—CH₂CH=CH₂ | N—CN | oily substance |
| 27 | C₂H₅ | n-C₃H₇ | —(CH₂)₂— | N—CH₂C≡CH | N—CN | oily substance |
| 28 | C₂H₅ | sec-C₄H₉ | —(CH₂)₂— | N—COCH₃ | N—CN | oily substance |
| 29 | C₂H₅ | sec-C₄H₉ | —(CH₂)₂— | N—CH₂OCH₃ | N—CN | oily substance |
| 30 | C₂H₅ | n-C₃H₇ | —CHCH₂— \| CH₃ | N—CH₂OC₂H₅ | N—CN | oily substance |
| 31 | C₂H₅ | n-C₃H₇ | —CH₂CCH₂— \| CH₃ / CH₃ | " | N—CN | oily substance |
| 32 | C₂H₅ | sec-C₄H₉ | —(CH₂)₂— | N—SO₂N(CH₃)₂ | N—CN | oily substance |
| 33 | C₂H₅ | n-C₃H₇ | —(CH₂)₂— | N—CH₂SCH₃ | N—CN | oily substance |
| 34 | C₂H₅ | n-C₃H₇ | —(CH₂)₂— | N—CH₃ | NCOCF₃ | oily substance |
| 35 | C₂H₅ | n-C₃H₇ | —(CH₂)₂— | N—C₂H₅ | C(CN)₂ | oily substance |
| 36 | C₂H₅ | n-C₃H₇ | —(CH₂)₂— | N-n-C₃H₇ | C(CN)₂ | oily substance |
| 37 | C₂H₅ | n-C₃H₇ | —(CH₂)₂— | NH | C(CN)COOC₂H₅ | oily substance |
| 38 | C₂H₅ | n-C₃H₇ | —(CH₂)₂— | N—CH₃ | C(CN)COOC₂H₅ | oily substance |
| 39 | C₂H₅ | n-C₃H₇ | —(CH₂)₂— | N—C₂H₅ | C(CN)COOC₂H₅ | oily substance |
| 40 | C₂H₅ | sec-C₄H₉ | —(CH₂)₂— | CH₂ | N—CN | oily substance |
| 41 | C₂H₅ | sec-C₄H₉ | —(CH₂)₂— | N—CH₃ | N—CN | m.p.: 76.0~80.0° C. |
| 42 | C₂H₅ | CH₃ | —(CH₂)₂— | N—CH₃ | N—CN | m.p.: 116.0~118.5° C. |
| 43 | C₂H₅ | C₂H₅ | —(CH₂)₂— | N—CH₃ | N—CN | oily substance |
| 44 | C₂H₅ | iso-C₄H₉ | —(CH₂)₂— | N—CH₃ | N—CN | oily substance |
| 45 | C₂H₅ | sec-C₄H₉ | —CHCH₂— \| CH₃ | O | N—CN | oily substance |
| 46 | C₂H₅ | n-C₃H₇ | —(CH₂)₂— | N—COOC₂H₅ | N—CN | oily substance |
| 47 | C₂H₅ | n-C₃H₇ | —(CH₂)₂— | N—CH₂CN | N—CN | oily substance |
| 48 | C₂H₅ | n-C₃H₇ | —(CH₂)₂— | N—SO₂CH₃ | N—CN | oily substance |
| 49 | C₂H₅ | n-C₃H₇ | —(CH₂)₂— | N—CH₂OCH₂CH₂OCH₃ | N—CN | oily substance |
| 50 | C₂H₅ | sec-C₄H₉ | —(CH₂)₂— | N—CON(CH₃)₂ | N—CN | oily substance |
| 51 | C₂H₅ | sec-C₄H₉ | —(CH₂)₂— | N-n-C₃H₇ | N—CN | oily substance |
| 52 | C₂H₅ | n-C₃H₇ | —(CH₂)₂— | N—CH₂OCH₃ | N—NO₂ | oily substance |
| 53 | C₂H₅ | sec-C₄H₉ | —(CH₂)₂— | N—CH₂OCH₃ | C(CN)₂ | oily substance |
| 54 | C₂H₅ | sec-C₄H₉ | —(CH₂)₂— | N—CO—C(CH₃)₂—CH₂Cl | C(CN)₂ | oily substance |

TABLE 1-continued

| Comp. No. | R¹ | R² | —A— | X | Z | Physical Property |
|---|---|---|---|---|---|---|
| 55 | $C_2H_5$ | $n\text{-}C_3H_7$ | $-(CH_2)_2-$ | $N-CH_2CO-C(CH_3)_3$ | $N-CN$ | oily substance |
| 56 | $C_2H_5$ | $n\text{-}C_3H_7$ | $-(CH_2)_3-$ | $N-CH_3$ | $N-CN$ | m.p.: 58.5~61.5° C. |
| 57 | $C_2H_5$ | $n\text{-}C_3H_7$ | $-(CH_2)_2-$ | $CH_2$ | $N-CN$ | oily substance |
| 58 | $C_2H_5$ | $n\text{-}C_3H_7$ | $-(CH_2)_2-$ | $CHCH_3$ | $N-CN$ | oily substance |
| 59 | $C_2H_5$ | $n\text{-}C_3H_7$ | $-(CH_2)_2-$ | $CH_2$ | $NNO_2$ | oily substance |
| 60 | $C_2H_5$ | $n\text{-}C_3H_7$ | $-(CH_2)_3-$ | $CH_2$ | $N-CN$ | m.p.: 44.0~47.0° C. |

TABLE 2

| Comp. No. | IR Spectra and NMR Spectra |
|---|---|
| 1 | IR (KBr): 1251 (P=O) cm$^{-1}$<br>NMR (CDCl$_3$), δ (ppm): 0.8~2.1 (m, 8H, OCH$_2$C$\underline{H}_3$, SCH$_2$C$\underline{H}_2$—CH$_3$), 2.7~3.2 (m, 2H, SCH$_2$), 3.0 (s, 3H, NCH$_3$), 3.8~4.5 (m, 6H, OCH$_2$, NCH$_2$CH$_2$N) |
| 2 | IR (neat): 1251 (P=O) cm$^{-1}$<br>NMR (CDCl$_3$), δ (ppm): 0.8~2.1 (m, 11H, OCH$_2$C$\underline{H}_3$, SCH$_2$CH$_2$C$\underline{H}_3$, NCH$_2$C$\underline{H}_3$), 2.7~3.75 (m, 4H, SCH$_2$, NCH$_2$), 3.8~4.5 (m, 6H, OCH$_2$, NCH$_2$CH$_2$N) |
| 3 | IR (neat): 2176 (C≡N), 1257 (P=O) cm$^{-1}$<br>NMR (CDCl$_3$), δ (ppm) 0.8~2.1 (m, 8H, OCH$_2$C$\underline{H}_3$, SCH$_2$C$\underline{H}_2$—CH$_3$), 2.7~3.2 (m, 2H, SCH$_2$), 3.3 (s, 3H, NCH$_3$), 3.5~4.5 (m, 6H, OCH$_2$, NCH$_2$CH$_2$N) |
| 4 | IR (neat): 2176 (C≡N), 1257 (P=O) cm$^{-1}$<br>NMR (CDCl$_3$), δ (ppm): 0.8~2.1 (m, 11H, OCH$_2$C$\underline{H}_3$, SCH$_2$—C$\underline{H}_2$CH$_3$, NCH$_2$C$\underline{H}_3$), 2.7~3.2 (m, 2H, SCH$_2$), 3.5~4.5 (m, 8H, OCH$_2$, NCH$_2$CH$_2$N, NCH$_2$) |
| 5 | IR (neat): 2170 (C≡N), 1257 (P=O) cm$^{-1}$<br>NMR (CDCl$_3$), δ (ppm): 0.8~2.1 (m, 13H, OCH$_2$C$\underline{H}_3$, SCH$_2$—C$\underline{H}_2$CH$_3$, NCH$_2$CH$_2$C$\underline{H}_3$), 2.7~3.2 (m, 2H, SCH$_2$), 3.4~4.5 (m, 8H, OCH$_2$, NCH$_2$CH$_2$N, NCH$_2$) |
| 6 | IR (neat): 2170 (C≡N), 1257 (P=O) cm$^{-1}$<br>NMR (CDCl$_3$), δ (ppm): 0.8~2.1 (m, 15H, OCH$_2$C$\underline{H}_3$, SCH$_2$—C$\underline{H}_2$CH$_3$, NCH$_2$CH$_2$CH$_2$C$\underline{H}_3$), 2.7~3.2 (m, 2H, SCH$_2$), 3.5~4.5 (m, 8H, SCH$_3$, NCH$_2$CH$_2$N, NCH$_2$) |
| 7 | IR (neat): 3232 (NH), 2194 (C≡N), 1257 (P=O) cm$^{-1}$<br>NMR (CDCl$_3$), δ (ppm): 0.8~2.1 (m, 8H, OCH$_2$C$\underline{H}_3$, SCH$_2$—C$\underline{H}_2$CH$_3$), 2.7~3.2 (m, 2H, SCH$_2$), 3.5~4.5 (m, 6H, OC$\underline{H}_2$NCH$_2$CH$_2$N), 8.00 (bs, 1H, NH) |
| 8 | IR (neat): 3376 (NH), 1257 (P=O) cm$^{-1}$<br>NMR (CDCl$_3$), δ (ppm): 0.8~2.1 (m, 8H, OCH$_2$C$\underline{H}_3$, SCH$_2$C$\underline{H}_2$CH$_3$), 2.36 (s, 3H, Ph—CH$_3$), 2.6~3.1 (m, 2H, SCH$_2$), 3.4~4.4 (m, 6H, OCH$_2$, NCH$_2$CH$_2$N), 7.1~7.9 (m, 5H, NH, benzene) |
| 9 | IR (neat): 3370 (NH), 1257 (P=O) cm$^{-1}$<br>NMR (CDCl$_3$), δ (ppm): 0.8~2.1 (m, 8H, OCH$_2$C$\underline{H}_3$, SCH$_2$—C$\underline{H}_2$CH$_3$), 2.7~3.2 (m, 2H, SCH$_2$), 2.93 (s, 3H, SO$_2$CH$_3$), 3.5~4.5 (m, 6H, OCH$_2$, NCH$_2$CH$_2$N), 7.34 (bs, 1H, NH) |
| 10 | IR (neat): 1257 (P=O) cm$^{-1}$<br>NMR (CDCl$_3$), δ (ppm): 0.8~2.1 (m, 8H, OCH$_2$C$\underline{H}_3$, SCH$_2$—C$\underline{H}_2$CH$_3$), 2.7~3.5 (m, 4H, SCH$_2$, SCH$_2$CH$_2$N), 2.99 (s, 3H, SO$_2$CH$_3$), 3.9~4.5 (m, 4H, OCH$_2$, SCH$_2$CH$_2$N) |
| 11 | IR (neat): 2176 (C≡N), 1257 (P=O) cm$^{-1}$<br>NMR (CDCl$_3$), δ (ppm): 0.8~2.1 (m, 8H, OCH$_2$C$\underline{H}_3$, SCH$_2$CH$_2$C$\underline{H}_3$) 2.7~4.7 (m, 8H, SCH$_2$, SCH$_2$CH$_2$N, OCH$_2$) |
| 12 | IR (neat): 1251 (P=O) cm$^{-1}$<br>NMR (CDCl$_3$), δ (ppm): 0.8~2.1 (m, 8H, OCH$_2$C$\underline{H}_3$, SCH$_2$—C$\underline{H}_2$CH$_3$), 2.7~3.4 (m, 4H, SCH$_2$, SCH$_2$CH$_2$N), 4.0~4.6 (m, 4H, OCH$_2$, SCH$_2$C$\underline{H}_2$N) |
| 13 | IR (neat): 2176 (C≡N), 1257 (P=O) cm$^{-1}$<br>NMR (CDCl$_3$), δ (ppm): 0.8~2.2 (m, 13H, OCH$_2$C$\underline{H}_3$, SCH—(C$\underline{H}_3$)CH$_2$CH$_3$, NCH$_2$CH$_2$C$\underline{H}_2$N), 3.1~4.5 (m, 7H, SCH, OCH$_2$, NCH$_2$CH$_2$N), 3.35 (s, 3H, NCH$_3$) |
| 14 | IR (neat): 2182 (C≡N), 1266 (P=O) cm$^{-1}$<br>NMR (CDCl$_3$), δ (ppm): 0.8~2.1 (m, 16H, OCH$_2$C$\underline{H}_3$, OCH$_2$—C$\underline{H}_3$, SCH$_2$CH$_2$C$\underline{H}_3$, SCH$_2$C$\underline{H}_2$CH$_3$), 2.6~3.2 (m, 4H, SCH$_2$, SCH$_2$), 3.9~4.5 (m, 8H, OCH$_2$, OCH$_2$, NCH$_2$CH$_2$N) |
| 15 | IR (neat): 2176 (C≡N), 1257 (P=O) cm$^{-1}$<br>NMR (CDCl$_3$), δ (ppm): 0.8~2.0 (m, 17H, OCH$_2$C$\underline{H}_3$, SCH—(C$\underline{H}_3$)CH$_2$CH$_3$, N—CH(C$\underline{H}_3$)$_2$), 3.2~4.5 (m, 7H, SCH, NCH$_2$—CH$_2$N, OCH$_3$), 4.7~5.2 (m, 1H, NCH) |
| 16 | IR (neat): 2176 (C≡N), 1254 (P=O) cm$^{-1}$<br>NMR (CDCl$_3$), δ (ppm): 0.8~2.0 (m, 11H, OCH$_2$C$\underline{H}_3$, SCH—(C$\underline{H}_3$)CH$_2$CH$_3$), 3.20~4.5 (m, 7H, SCH, NCH$_2$CH$_2$N, OCH$_2$), 3.32 (s, 3H, NCH$_3$) |
| 17 | IR (neat): 2200 (C≡N), 1263 (P=O) cm$^{-1}$<br>NMR (CDCl$_3$), δ (ppm): 0.8~2.0 (m, 8H, OCH$_2$C$\underline{H}_3$, SCH$_2$—C$\underline{H}_2$CH$_3$), 2.1~3.7 (m, 8H, NCH$_2$CH$_2$CH$_2$N, SCH$_2$), 3.35 (s, 3H, NCH$_3$), 3.9~4.5 (m, 2H, OCH$_2$) |
| 18 | IR (neat): 2200 (C≡N), 1269 (P=O) cm$^{-1}$<br>NMR (CDCl$_3$), δ (ppm): 0.8~2.0 (m, 8H, OCH$_2$C$\underline{H}_3$, SCH$_2$—C$\underline{H}_2$CH$_3$), 2.6~4.5 (m, 8H, SCH$_3$, NCH$_2$CH$_2$N, OCH$_2$), 3.30 (s, 3H, NCH$_3$) |
| 19 | IR (neat): 1617 (C=N) cm$^{-1}$<br>NMR (CDCl$_3$), δ (ppm): 0.8~2.0 (m, 8H, OCH$_2$C$\underline{H}_3$, SCH$_2$—C$\underline{H}_2$CH$_3$), 2.6~4.5 (m, 8H, SCH$_2$, NCH$_2$CH$_2$N, OCH$_2$), 2.97 (s, 3H, SO$_2$CH$_3$), 3.30 (s, 3H, NCH$_3$) |
| 20 | IR (KBr): 2200 (C≡N), 1265 (P=O) cm$^{-1}$<br>NMR (CDCl$_3$), δ (ppm): 0.8~2.0 (m, 11H, OCH$_2$C$\underline{H}_3$, SCH—(C$\underline{H}_3$)CH$_2$CH$_3$), 3.20~4.5 (m, 7H, SCH, NCH$_2$CH$_2$N, OCH$_2$), 3.30 (s, 3H, NCH$_3$) |
| 21 | IR (neat): 3274 (NH), 1248 (P=O) cm$^{-1}$<br>NMR (CDCl$_3$), δ (ppm): 0.8~2.0 (m, 8H, OCH$_2$C$\underline{H}_3$, SCH$_2$—C$\underline{H}_2$CH$_3$), 2.56 (s, 3H, NCH$_3$), 2.70~3.20 (m, 2H, SCH$_2$), 3.9~4.7 (m, 6H, OCH$_2$, NCH$_2$N, NCH$_2$N), 9.49 (bs, 1H, NH) |
| 22 | IR (neat): 1248 (P=O) cm$^{-1}$<br>NMR (CDCl$_3$), δ (ppm): 0.8~2.0 (m, 8H, OCH$_2$C$\underline{H}_3$, SCH$_2$—C$\underline{H}_2$CH$_3$), 2.58 (s, 3H, NCH$_3$), 3.0 (s, 3H, NCH$_3$), 2.70~3.2 (m, 2H, SCH$_2$), 3.8~4.5 (m, 6H, NCH$_2$N, NCH$_2$N) |
| 24 | IR (neat): 1572 (C=N), 1251 (P=O) cm$^{-1}$<br>NMR (CDCl$_3$), δ (ppm): 0.8~2.0 (m, 8H, OCH$_2$C$\underline{H}_3$, SCH$_2$—C$\underline{H}_2$CH$_3$), 2.7~3.2 (m, 2H, SCH$_2$), 3.7~4.5 (m, 8H, OCH$_2$, NCH$_2$CH=CH$_2$, NCH$_2$CH$_2$N), 5.1~6.0 (m, 3H, NCH$_2$C$\underline{H}$=CH$_2$) |
| 25 | IR (neat): 1515 (C=N), 1248 (P=O) cm$^{-1}$ |

TABLE 2-continued

| Comp. No. | IR Spectra and NMR Spectra |
|---|---|
| | NMR (CDCl$_3$), δ (ppm): 0.8~2.0 (m, 8H, OCH$_2$CH$_3$, SCH$_2$—CH$_2$CH$_3$), 2.7~3.2 (m, 2H, SCH$_2$), 3.13 (s, 3H, NCH$_3$) 3.6~4.5 (m, 6H, OCH$_2$, NCH$_2$CH$_3$N) |
| 26 | IR (neat): 2176 (C≡N), 1257 (P=O) cm$^{-1}$<br>NMR (CDCl$_3$), δ (ppm): 0.8~2.0 (m, 8H, OCH$_2$CH$_3$, SCH$_2$—CH$_2$CH$_3$), 2.7~3.2 (m, 2H, SCH$_2$), 3.6~4.5 (m, 8H, OCH$_2$, NCH$_2$CH=CH$_2$, NCH$_2$CH$_2$N), 5.1~6.0 (m, 3H, NCH$_2$CH=CH$_2$) |
| 27 | IR (neat): 3232 (C≡CH), 2182 (C≡N), 1257 (P=O) cm$^{-1}$<br>NMR (CDCl$_3$), δ (ppm): 0.8~2.0 (m, 8H, OCH$_2$CH$_3$, SCH$_2$—CH$_2$CH$_3$), 2.38 (t, 1H, CH$_2$C≡CH), 2.7~3.2 (m, 2H, SCH$_2$), 3.6~4.5 (m, 6H, OCH$_2$, NCH$_2$CH$_2$N), 5.55 (d, 2H, NCH$_2$C≡CH) |
| 28 | IR (neat): 2188 (C≡N), 1737 (C=O), 1257 (P=O) cm$^{-1}$<br>NMR (CDCl$_3$), δ (ppm): 0.8~2.0 (m, 11H, OCH$_2$CH$_3$, SCH—(CH$_3$)CH$_2$CH$_3$), 2.54 (s, 3H, COCH$_3$), 3.2~4.7 (m, 7H, SCH, NCH$_2$CH$_2$N, OCH$_2$) |
| 29 | IR (neat): 2182 (C≡N), 1257 (P=O) cm$^{-1}$<br>NMR (CDCl$_3$), δ (ppm) 0.8~2.0 (m, 11H, OCH$_2$CH$_3$, SCH—(CH$_3$)CH$_2$CH$_3$), 3.2~4.5 (m, 7H, SCH, NCH$_2$CH$_2$N, OCH$_2$), 3.41 (s, 3H, CH$_3$O), 5.11 (s, 2H, NCH$_2$O) |
| 30 | IR (neat): 2182 (C≡N), 1260 (P=O) cm$^{-1}$<br>NMR (CDCl$_3$) δ (ppm): 0.8~2.0 (m, 14H, OCH$_2$CH$_3$, SCH$_2$—CH$_2$CH$_3$, OCH$_2$CH$_3$), NCH(CH$_3$)CH$_2$N), 2.7~4.5 (m, 9H, SCH$_2$, OCH$_2$, OCH$_2$, NCH(CH$_3$)CH$_2$N), 5.14 (s, 2H, NCH$_2$O) |
| 31 | IR (neat): 2176 (C≡N), 1272 (P=O) cm$^{-1}$<br>NMR (CDCl$_3$), δ (ppm): 0.8~2.0 (m, 17H, OCH$_2$CH$_3$, SCH$_2$—CH$_2$CH$_3$, OCH$_2$CH$_3$, NCH$_2$C(CH$_3$)$_2$CH$_2$N), 2.6~4.5 (m, 10H, SCH$_2$, OCH$_2$, OCH$_2$, NCH$_2$C(CH$_3$)$_2$CH$_2$N), 5.16 (s, 2H, NCH$_2$O) |
| 32 | IR (neat): 2188 (C≡N), 1263 (P=O) cm$^{-1}$<br>NMR (CDCl$_3$), δ (ppm): 0.8~2.0 (m, 11H, OCH$_2$CH$_3$, SCH—(CH$_3$)CH$_2$CH$_3$), 2.95 (s, 6H, SO$_2$N(CH$_3$)$_2$), 3.2~4.5 (m, 7H, SCH, NCH$_2$CH$_2$N, OCH$_2$) |
| 33 | IR (neat): 2176 (C≡N), 1266 (P=O) cm$^{-1}$<br>NMR (CDCl$_3$), δ (ppm): 0.8~2.0 (m, 8H, OCH$_2$CH$_3$, SCH$_2$—CH$_2$CH$_3$) 2.25 (s, 3H, SCH$_3$), 2.7~3.2 (m, 2H, SCH$_2$), 3.6~4.5 (m, 6H, NCH$_3$CH$_2$N, OCH$_2$), 4.90 (s, 2H, SCH$_2$N) |
| 34 | IR (neat): 1662 (C=O), 1599 (C=N), 1257 (P=O) cm$^{-1}$<br>NMR (CDCl$_3$), δ (ppm): 0.8~2.0 (m, 8H, OCH$_2$CH$_3$, SCH$_2$—CH$_2$CH$_3$), 2.6~3.2 (m, 2H, SCH$_2$), 2.91 (s, 3H, NCH$_3$), 3.6~4.5 (m, 6H, NCH$_2$CH$_2$N, OCH$_2$) |
| 35 | IR (neat): 2200 (C≡N), 1263 (P=O) cm$^{-1}$<br>NMR (CDCl$_3$), δ (ppm): 0.8~2.0 (m, 11H, OCH$_2$CH$_3$, SCH$_3$—CH$_2$CH$_3$, NCH$_2$CH$_3$), 2.6~3.2 (m, 2H, SCH$_2$), 3.5~4.5 (m, 8H, NCH$_2$, NCH$_2$CH$_2$N, OCH$_2$) |
| 36 | IR (neat): 2200 (C≡N), 1265 (P=O) cm$^{-1}$<br>NMR (CDCl$_3$), δ (ppm): 0.8~2.0 (m, 13H, OCH$_2$CH$_3$, SCH$_2$—CH$_2$CH$_3$, NCH$_2$CH$_2$CH$_3$), 2.6~3.2 (m, 2H, SCH$_2$), 3.5~4.5 (m, 8H, NCH$_2$, NCH$_2$CH$_2$N, OCH$_2$) |
| 37 | IR (neat): 3292 (NH), 2200 (C≡N), 1671 (C=O), 1254 (P=O) cm$^{-1}$<br>NMR (CDCl$_3$), δ (ppm): 0.8~2.0 (m, 11H, OCH$_2$CH$_3$, SCH$_2$—CH$_2$CH$_3$, COOCH$_2$CH$_3$), 2.6~3.2 (m, 2H, SCH$_2$) 3.5~4.5 (m, 8H, NCH$_2$CH$_2$N, COOCH$_2$CH$_3$, OCH$_2$), 9.43 (bs, 1H, NH) |
| 38 | IR (neat): 2188 (C≡N), 1686 (C=O), 1257 (P=O) cm$^{-1}$<br>NMR (CDCl$_3$), δ (ppm): 0.8~2.0 (m, 11H, OCH$_2$CH$_3$, SCH$_2$—CH$_2$CH$_3$, COOCH$_2$CH$_3$), 2.6~3.2 (m, 2H, SCH$_2$), 3.15 (s, 3H, NCH$_3$), 3.4~4.5 (m, 8H, NCH$_2$CH$_2$N, COOCH$_2$—CH$_3$, OCH$_2$) |
| 39 | IR (neat): 2188 (C≡N), 1686 (C=O), 1257 (P=O) cm$^{-1}$<br>NMR (CDCl$_3$), (ppm): 0.8~2.0 (m, 14H, OCH$_2$CH$_3$, SCH$_2$—CH$_2$CH$_3$, NCH$_2$CH$_3$, COOCH$_2$CH$_3$), 2.6~3.2 (m, 2H, SCH$_2$), 3.4~4.5 (m, 10H, NCH$_2$CH$_2$N, NCH$_2$, COOCH$_2$CH$_3$, OCH$_2$) |
| 40 | IR (neat): 2188 (C≡N), 1608 (C=N), 1254 (P=O) cm$^{-1}$<br>NMR (CDCl$_3$), δ (ppm): 0.8~2.3 (m, 13H, OCH$_2$CH$_3$, SCH—(CH$_3$)CH$_2$CH$_3$, NCH$_2$CH$_2$CH$_2$C=NCN), 2.8~4.4 (m, 7H, NCH$_2$CH$_2$CH$_2$C=NCN, SCH, OCH$_2$) |
| 41 | IR (KBr): 2176 (C≡N), 1254 (P=O) cm$^{-1}$<br>NMR (CDCl$_3$), δ (ppm): 0.8~2.0 (m, 8H, SCH(CH$_3$)CH$_2$CH$_3$), 3.32 (s, 3H, NCH$_3$), 3.2~3.9 (m, 5H, SCH, NCH$_2$CH$_2$N), 3.81 (d, 3H, OCH$_3$) |
| 42 | IR (KBr): 2176 (C≡N), 1254 (P=O) cm$^{-1}$<br>NMR (CDCl$_3$), δ (ppm): 1.35 (t, 3H, OCH$_2$CH$_3$), 2.40 (d, 3H, SCH$_3$), 3.32 (s, 3H, NCH$_3$), 3.6~4.5 (m, 6H, N—CH$_2$CH$_2$N, OCH$_2$) |
| 43 | IR (neat): 2176 (C≡N), 1254 (P=O) cm$^{-1}$<br>NMR (CDCl$_3$), δ (ppm): 1.35 (t, 6H, OCH$_2$CH$_3$, SCH$_2$CH$_3$), 2.6~3.2 (m, 2H, SCH$_2$), 3.32 (s, 3H, NCH$_3$), 3.6~4.5 (m, 6H, NCH$_2$CH$_2$N, OCH$_2$) |
| 44 | IR (neat): 2176 (C≡N), 1260 (P=O) cm$^{-1}$<br>NMR (CDCl$_3$), δ (ppm): 0.9~2.1 (m, 10H, OCH$_2$CH$_3$, SCH$_2$—CH(CH$_3$)$_2$), 2.7~3.1 (m, 2H, SCH$_2$), 3.32 (s, 3H, NCH$_3$), 3.6~4.5 (m, 6H, NCH$_2$CH$_2$N, OCH$_2$) |
| 45 | IR (neat): 2212 (C≡N), 1260 (P=O) cm$^{-1}$<br>NMR (CDCl$_3$), δ (ppm): 0.8~2.0 (m, 14H, OCH$_2$CH$_3$, SCH—(CH$_3$)CH$_2$CH$_3$, OCH(CH$_3$)CH$_2$N), 3.2~4.5 (m, 5H, SCH, OCH(CH$_3$)CH$_2$N, OCH$_2$), 4.8~5.4 (m, 1H, OCH(CH$_3$)CH$_2$N) |
| 46 | IR (neat): 2194 (C≡N), 1764 (C=O) cm$^{-1}$<br>NMR (CDCl$_3$), δ (ppm): 0.8~2.0 (m, 11H, OCH$_2$CH$_3$, SCH$_2$—CH$_2$CH$_3$, COOCH$_2$CH$_3$), 2.72~3.26 (m, 2H, SCH$_2$), 3.8~4.5 (m, 8H, NCH$_2$CH$_2$N, OCH$_2$, COOCH$_2$CH$_3$) |
| 47 | IR (neat): 2182 (C≡N), 1260 (P=O) cm$^{-1}$<br>NMR (CDCl$_3$), δ (ppm): 0.8~2.0 (m, 8H, OCH$_2$CH$_3$, SCH$_2$—CH$_2$CH$_3$), 2.70~3.22 (m, 2H, SCH$_2$), 3.6~4.5 (m, 6H, NCH$_2$CH$_2$N, OCH$_2$), 4.62 (s, 2H, NCH$_2$CN) |
| 48 | IR (neat): 2188 (C≡N), 1260 (P=O) cm$^{-1}$<br>NMR (CDCl$_3$), δ (ppm): 0.8~2.0 (m, 8H, OCH$_2$CH$_3$, SCH$_2$—CH$_2$CH$_3$), 2.6~3.2 (m, 2H, SCH$_2$), 3.45 (s, 3H, SO$_2$CH$_3$) 3.6~4.5 (m, 6H, NCH$_2$CH$_2$N, OCH$_2$) |
| 49 | IR (neat): 2182 (C≡N), 1257 (P=O) cm$^{-1}$<br>NMR (CDCl$_3$), δ (ppm): 0.8~2.0 (m, 8H, OCH$_2$CH$_3$, SCH$_2$—CH$_2$CH$_3$), 2.7~3.2 (m, 2H, SCH$_2$), 3.35 (s, 3H, OCH$_3$), 3.4~4.5 (m, 10H, NCH$_2$CH$_2$N, OCH$_2$CH$_2$O, OCH$_2$CH$_3$), 5.20 (s, 2H, OCH$_2$N) |
| 50 | IR (neat): 2182 (C≡N), 1710 (C=O) cm$^{-1}$ |

TABLE 2-continued

| Comp. No. | IR Spectra and NMR Spectra |
|---|---|
| | NMR (CDCl$_3$), δ (ppm) 0.8~2.0 (m, 11H, OCH$_2$CH$_3$, SCH—(CH$_3$)CH$_2$CH$_3$), 3.05 (s, 6H, N(CH$_3$)$_2$), 3.2~4.5 (m, 7H, SCH, NCH$_2$CH$_2$N, OCH$_2$) |
| 51 | IR (neat): 2176 (C≡N), 1254 (P=O) cm$^{-1}$<br>NMR (CDCl$_3$), δ (ppm): 0.8~2.0 (m, 16H, OCH$_2$CH$_3$, SCH—(CH$_3$)CH$_2$CH$_3$, NCH$_2$CH$_2$CH$_3$), 3.2~4.5 (m, 9H, SCH, NCH$_2$CH$_2$N, NCH$_2$, OCH$_2$) |
| 52 | IR (neat): 1563 (C=N), 1248 (P=O) cm$^{-1}$<br>NMR (CDCl$_3$), δ (ppm): 0.8~2.0 (m, 8H, OCH$_2$CH$_3$, SCH$_2$—CH$_2$CH$_3$), 2.7~4.5 (m, 8H, SCH$_2$, NCH$_2$CH$_2$N, OCH$_2$), 3.32 (s, 3H, OCH$_3$), 4.70 (s, 2H, OCH$_2$N) |
| 53 | IR (neat): 2206 (C≡N), 1560 (C=C) cm$^{-1}$<br>NMR (CDCl$_3$), δ (ppm): 0.8~2.0 (m, 11H, OCH$_2$CH$_3$, SCH—(CH$_3$)CH$_2$CH$_3$), 3.2~4.5 (m, 7H, SCH, NCH$_2$CH$_2$N, OCH$_2$), 3.39 (s, 3H, OCH$_3$), 5.01 (s, 2H, OCH$_2$N) |
| 54 | IR (neat): 2212 (C≡N), 1719 (C=O), 1563 (C=C) cm$^{-1}$<br>NMR (CDCl$_3$), δ (ppm): 0.8~2.0 (m, 17H, OCH$_2$CH$_3$, SCH—(CH$_3$)CH$_2$CH$_3$, NCOC(CH$_3$)$_3$), 3.2~3.8 (m, 3H, SCH, CH$_2$Cl), 4.0~4.5 (m, 6H, OCH$_2$, NCH$_2$CH$_2$N) |
| 55 | IR (neat): 2176 (C≡N), 1722 (C=O), 1617 (C=N) cm$^{-1}$<br>NMR (CDCl$_3$), δ (ppm): 0.8~2.1 (m, 8H, OCH$_2$CH$_3$, SCH$_2$—CH$_2$CH$_3$), 1.21 (s, 9H, C(CH$_3$)$_3$), 2.7~4.8 (m, 10H, OCH$_2$, SCH$_2$, NCH$_2$CH$_2$N, NCH$_2$CO) |
| 56 | IR (neat): 2170 (C≡N), 1590 (C=N) cm$^{-1}$<br>NMR (CDCl$_3$), δ (ppm): 0.8~2.2 (m, 10H, OCH$_2$CH$_3$, SCH$_2$—CH$_2$CH$_3$, NCH$_2$CH$_2$N), 2.6~4.5 (m, 8H, SCH$_2$, OCH$_2$, NCH$_2$CH$_2$N), 3.37 (s, 3H, NCH$_3$) |
| 57 | IR (neat): 2188 (C≡N), 1608 (C=N), 1257 (P=O) cm$^{-1}$<br>NMR (CDCl$_3$), δ (ppm): 0.8~2.4 (m, 10H, OCH$_2$CH$_3$, SCH$_2$—CH$_2$CH$_3$, NCH$_2$CH$_2$CH$_2$C̲=NCN), 2.7~3.2 (m, 4H, SCH$_2$, NCH$_2$CH$_2$CH$_2$C̲=NCN), 3.8~4.5 (m, 4H, OCH$_2$, NCH$_2$CH$_2$—CH$_2$C̲=NCN) |
| 58 | IR (neat): 2188 (C≡N), 1605 (C=N), 1257 (P=O) cm$^{-1}$<br>NMR (CDCl$_3$), δ (ppm): 0.8~3.4 (m, 16H, OCH$_2$CH$_3$, SCH$_2$—CH$_2$CH$_3$, NCH$_2$CH$_2$CH(CH$_3$)C̲=NCN), 3.7~4.5 (m, 4H, OCH$_2$, NCH$_2$CH$_2$CHCH$_3$C̲=NCN) |
| 59 | IR (neat): 1542 (C=N), 1263 (P=O) cm$^{-1}$<br>NMR (CDCl$_3$), δ (ppm): 0.8~2.4 (m, 10H, OCH$_2$CH$_3$, SCH$_2$—CH$_2$CH$_3$, NCH$_2$CH$_2$CH$_2$C̲=NCN), 2.7~3.3 (m, 4H, SCH$_2$, NCH$_2$CH$_2$CH$_2$C̲=NCN), 3.7~4.5 (m, 4H, OCH$_2$, NCH$_2$CH$_2$—CH$_2$C̲=NCN) |
| 60 | IR (neat): 2182 (C≡N), 1563 (C=N), 1254 (P=O) cm$^{-1}$<br>NMR (CDCl$_3$), δ (ppm): 0.8~2.1 (m, 12H, OCH$_2$CH$_3$, SCH$_2$—CH$_2$CH$_3$, —NCH$_2$CH$_2$CH$_2$CH$_2$C̲=NCN), 2.6~3.2 (m, 4H, SCH$_2$, —NCH$_2$CH$_2$CH$_2$CH$_2$C̲=NCN), 3.6~4.5 (m, 4H, OCH$_2$, —NCH$_2$CH$_2$—CH$_2$CH$_2$C̲=NCN) |

The compounds of the present invention exhibit excellent activity as active ingredients of insecticides, acaricides and nematocides. The compounds of the present invention are effective for controlling, for instance, agricultural and horticultural pests such as Coleoptera (for instance, Scarabaeidae, Chrysomelidae, Henosepilachna vigintioctopunctata and Lissorhoptrus oryzophilus), Lepidoptera (for instance, Mamestra brassicae, Pieris rapae, Plutera xylostella, Noctuidae) Adoxophyes orana and Chilo suppressalis), Hemiptera (for instance, Delphacidae, Deltocephalidae, Aleyrodidae, Aphididae and Scales) and Thysanoptera (for instance, Scirtothrips dorsalis and Thrips pulmi); Sanitary pests such as Mosquitoes, Flies, Blattidae, Fleas and Lice; Grain pests; cloth and house pests; Plant parasitic nematodes such as root-knot nematodes and root-lesion nematodes; and Plant parasitic mites such as Tetranychus urticae, Tetranychus cinnabarinus, Tetranychus kanzawai and Panonychus citri. They are also effective for controlling soil insect pests. The term "soil insect pest" used herein means, for instance, Gastropoda such as slugs and snails; Isopoda such as Armadillidium vulgare and Sow bugs. In addition, they are likewise effective for controlling insect pest such as Dicofol, organophosphorus compound-resistant plant parasitic mites, organophosphorus compound-resistant Aphididae and Musca domestica.

When the compounds of the present invention are used as active ingredients of insecticidal, acaricidal, nematocidal compositions and composition for killing or controlling soil pest insect, they may be used as such, but may in general be formed into a variety of formulations together with adjuvants such as emulsifiable concentrates, dusts, wettable powders, liquid formulations, aerosols and pastes like conventional formulations of agricultural chemicals. The formulations in general comprise 0.5 to 90 parts by weight of the active ingredient and 10 to 99.5 parts by weight of an adjuvant. When these formulations are practically used, they can be applied as such or after diluting them with a diluent such as water to a desired concentration.

The term "adjuvant" herein means carriers, emulsifying agents, suspending agents, dispersing agents, spreaders, penetrants, wetting agents, thickeners and stabilizers. These adjuvants may, if necessary, be added in an appropriate amount. The carriers can roughly be classified into solid carriers and liquid carriers. Examples of the solid carriers include vegetable and animal powder such as starches, active carbon, soybean flour, wheat flour, wood powder, fish meal and powdered milk; and mineral powders such as talc, kaolin, bentonite, calcium carbonate, zeolite, diatomaceous earth, white carbon, clay, alumina and powdered sulfur. On the other hand, examples of the liquid carriers are water; alcohol is such as methyl alcohol and ethylene glycol; ketones such as acetone and methyl ethyl ketone; ethers such as dioxane and tetrahydrofuran; aliphatic hydrocarbons such as kerosine; aromatic hydrocarbons such as xylene, trimethylbenzene, tetramethylbenzene, cyclohexane and solvent naphtha; halogenated hydrocarbons such as chloroform and chlorobenzene; amides such as dimethylformamide; esters such as ethyl acetate and glycerin esters of fatty acids; nitriles such as acetonitrile; and sulfur atom-containing compounds such as dimethylsulfoxide. If necessary, the compounds of the present invention may be admixed with or used simultaneously with other agricultural chemicals such as insecticides, acaricides, nematocides, bactericides, antiviral agents, attractants, herbicides and plant growth regulators. In admixtures, greater effectiveness may sometimes be attained.

Examples of insecticides, acaricides or nematocides include organophosphorus acid ester compounds such as DDVP, Diazinon, Malathion, Fenitrothion, Prothiofos, Dioxabenzofos and Acephate; carbamate compounds such as Carbaryl, Propoxur, Oxamyl, Carbofuran and Methomyl; organochlorine compounds such as Dicofol and Tetradifon; organometal compounds such as Cyhexatin and Fenbutatin oxide; pyrethroid compounds such as Fenvalerate, Permethrin, Deltamethrin and Bifenthrin; urea compounds such as Diflubenzuron, Teflubenzuron and Chlorfluazuron; heterocyclic compounds such as Buprofezin and Hexythiazox; and other compounds such as dinitro compounds, organosulfur compounds, amidine compounds and triazine compounds. In addition to the foregoing compounds, the compound of the present invention can also be admixed with or used simultaneously with microbial pesticides such as BT agents and insect pathogen virus pesticides.

Examples of the bactericides are organophosphorus compounds such as Iprobenfos, Edifenphos and Phosethyl-aluminum; organocopper compounds such as oxyquinoline copper, copper terephthalate; organochlorine compounds such as Fthalide and Chlorothalonil; dithiocarbamate compounds such as Maneb, Zineb and Propineb; dicarboximide compounds such as Iprodione, Vinclozolin and Procymidone; azole compounds such as Triadimefon, Bitertanol, Etaconazole, Propiconazole and Penconazole; benzimidazole compounds such as Thiophanate-methyl and Benomyl; carbinol compounds such as Fenarimol and Flutriafol; benzanilide compounds such as Mepronil and Flutolanil; phenylamide compounds such as Metalaxyl and Oxadixyl; and other compounds such as piperazine compounds, quinoxaline compounds, morpholine compounds, anthraquinone compounds, sulfenic acid compounds, crotonic acid compounds, urea compounds and antibiotics.

As has been discussed above, the insecticides, acaricides and nematocides which comprise, as active ingredient, the compounds of the present invention are effective for controlling a variety of deleterious insects, harmful mites, destructive nematodes and harmful soil insect pests. These agricultural chemicals or formulations are applied at a concentration ranging from 1 to 20,000 ppm, desirably 20 to 2,000 ppm expressed in terms of the amount of the active ingredient. The concentration of these active ingredients can be appropriately adjusted depending on various factors such as shapes of the formulations, methods, purposes, time and places of application as well as the condition of infestation of insect pest. For instance, when aquatic insect pests are to be controlled, the insect pest can be controlled by spraying a solution of the compound having a concentration falling within the range defined above and, therefore, the concentration of the active ingredient required for controlling the aquatic insect pest is lower than that defined above. The amount of the agricultural chemicals or formulations to be applied per unit area (per 10 a) ranges from about 0.1 to 5,000 g and preferably 10 to 1,000 g expressed in terms of the amount of the active ingredient, but in a particular case, they may be applied in an amount outside the range defined above.

The application of a variety of formulations or dilute solutions thereof which comprise the compounds of the present invention can be performed according to any manner of application usually adopted, for instance, spraying (such as spraying, dusting, misting, atomizing, granule application and application on water surface); soil applications (such as mixing and drench); surface applications (such as coating, dressing and painting); and poison bait. It is also possible to control the development and growth of harmful insect pests, in particular deletrious insects through the action of excreta obtained by admixing the foregoing active ingredient to feed and giving the feed to domestic animals. Further, they can also be applied in accordance with ultra low volume application. In this method, the chemicals or formulations can comprise 100% active ingredient.

EXAMPLES

The method for preparing the compounds of the present invention will hereinafter be explained in more detail with reference to the following Preparation Examples.

Preparation Example 1:
O-ethyl-S-n-propyl-(3-ethyl-2-nitroimino-1-imidazolidinyl)phosphonothiolate (Compound No; 2)

2.00 g of O-ethyl-S-n-propyl-(2-nitroimino-1-imidazolidinyl) phosphonothiolate was dissolved in 20 ml of N,N-dimethylformamide and then 0.32 g of a 60% sodium hydride was gradually added to the resulting solution. Thereafter, the solution was cooled down to 0° to 5° C. and 1.27 g of ethyl iodide was gradually added thereto dropwise. After the completion of the dropwise addition, the temperature of the solution was slowly brought back to room temperature and the solution was further stirred for additional 12 hours to complete the reaction. After the reaction, the solution was poured into ice water and extracted with dichloromethane. The dichloromethane phase was washed with water, dried over anhydrous magnesium sulfate, the dichloromethane was distilled off under reduced pressure and the residue obtained was purified by silica gel column chromatography (eluent: ethyl acetate) to give 0.50 g of Compound No. 2 as an oily substance.

Preparation Example 2:
O-ethyl-S-n-propyl-(3-methyl-2-cyanoimino-1-imidazolidinyl)phosphonothiolate (Compound No. 3)

To a mixture comprising 0.44 g of a 60% sodium hydride and 50 ml of N,N-dimethylformamide, 1.24 g of 1-methyl-2-cyanoiminoimidazolidine was gradually added. After the mixture was allowed to stand for a brief period, 2.76 g of an 88.2% toluene solution of O-ethyl-S-n-propylphosphorochloride thiolate was gradually dropwise added to the mixture. After the completion of the dropwise addition, the reaction solution was poured into ice water and then extracted with chloroform. The chloroform phase was washed with water, dried over anhydrous magnesium sulfate, the chloroform was distilled off under reduced pressure and the residue obtained was purified by silica gel column chromatography (eluent: chloroform/methanol=97:3) to give 1.50 g of Compound No. 3 as an oily substance.

Preparation Example 3:
O-ethyl-S-n-propyl-(2-methanesulfonylimino-1-imidazolidinyl)phosphonothiolate (Compound No. 9)

2.0 g of 2-methanesulfonyliminoimidazolidine was dissolved in 20 ml of N,N-dimethylformamide. The resulting solution was cooled down to 0° C. and then 1.02 g of a 60% sodium hydride was gradually added. Thereafter, 3.00 g of an 88.2% toluene solution of O-ethyl-S-n-propylphosphorochloride thiolate was gradually dropwise added to the solution. After the completion of the dropwise addition, the temperature of the reaction solution was slowly brought back to room temperature and further the reaction was continued for additional 12 hours. After the reaction, the reaction solution was poured into ice water, neutralized with a 10% hydrochloric acid solution and then extracted with chloroform. The chloroform phase was washed with water, dried over anhydrous magnesium sulfate, the chloroform was distilled off under reduced pressure and the residue obtained was purified by silica gel column chromatography (eluent: chloroform/methanol=97:3) to give 2.20 g of Compound No. 9 as an oily substance.

Preparation Example 4:
O-ethyl-S-sec-butyl-(3-methoxymethyl-2-cyanoimino-1-imidazolidinyl)phosphonothiolate (Compound No. 29)

1.50 g of O-ethyl-S-sec-butyl-(2-cyanoimino-1-imidazolidinyl) phosphonothiolate was dissolved in 20 ml of tetrahydrofuran. The resulting solution was cooled and maintained at a temperature of ranging from 0° to 5° C. and 0.25 g of a 60% sodium hydride was gradually added to the solution. After 30 minutes, 0.50 g of chloromethyl methyl ether was dropwise added thereto. After the completion of the dropwise addition, the temperature of the reaction solution was brought back to room temperature and the solution was stirred for additional 3 hours to complete the reaction.

After the reaction, the reaction solution was poured into ice water and then extracted with ethyl acetate. The ethyl acetate phase was washed with water, dried over anhydrous magnesium sulfate, the ethyl acetate was distilled off under reduced pressure and the residue obtained was purified by silica gel column chromatography (eluent: chloroform) to thus give 1.10 g of Compound No. 29 as an oily substance.

Specific examples of formulations will be described below, but the adjuvants such as carriers and surfactants are by no means limited to those used in the following examples. In the following specific formulations, the term "part" means "part by weight" unless otherwise specified.

Formulation Example 1 (Wettable Powder)

20 parts of Compound No. 1, 56 parts of acid clay, 15 parts of white carbon, 4 parts of calcium lignin sulfonate and 5 parts of polyoxyethylene alkylphenyl ether were uniformly mixed and pulverized to give a wettable powder.

Formulation Example 2 (Emulsifiable Concentrate)

To 20 parts of Compound No. 2, 75 parts of xylene was added. And then, 5 parts of New Calgen ST-20 (available from Takemoto Oil & Fat Co., Ltd.) was added to the resulting solution as an emulsifying agent and then the mixture was mixed and dissolved to give an emulsifiable concentrate.

Formulation Example 3 (Granule)

5 parts of Compound No. 1, 3 parts of calcium lignin sulfonate, one part of sodium dodecylbenzenesulfonate, 30 parts of bentonite and 61 parts of clay were sufficiently pulverized and mixed. The mixture was then sufficiently kneaded while adding water, followed by granulation and drying to thus give a granule.

The insecticidal, acaricidal and nematocidal effects of the compounds of the present invention will hereunder be explained with reference to the following Test Examples.

Test Example 1

The emulsifiable concentrate obtained by Formulation Example 2 was diluted with water to 500 ppm and 50 ppm and the resulting diluted emulsions were sprayed on leaves of chinese cabbage. After air-drying, the leaves were introduced into a plastic container having a size of 21 cm (height)×13 cm (width)×3 cm (depth), then 10 third instar larvae of common cutworm were put on the leaves. The container was then placed in a thermostated room maintained at 26° C. After 2 days, the number of surviving larvae was recorded to obtain the mortality (%) (repeated two times). The results thus obtained are summarized in the following Table 3.

TABLE 3

| Compound No. | Concn. of Active Ingredient (ppm) | Mortality (%) |
|---|---|---|
| 2 | 500 | 100 |
|  | 50 | 0 |
| 3 | 500 | 100 |
|  | 50 | 70 |
| 4 | 500 | 100 |
|  | 50 | 70 |
| 5 | 500 | 100 |
|  | 50 | 90 |
| 6 | 500 | 100 |
|  | 50 | 100 |
| 7 | 500 | 100 |
|  | 50 | 100 |
| 9 | 500 | 100 |
|  | 50 | 80 |
| 10 | 500 | 100 |
|  | 50 | 0 |
| 14 | 500 | 100 |
|  | 50 | 100 |
| 15 | 500 | 100 |
|  | 50 | 90 |
| 16 | 500 | 100 |
|  | 50 | 20 |
| 17 | 500 | 100 |
|  | 50 | 60 |
| 18 | 500 | 100 |
|  | 50 | 100 |
| 20 | 500 | 100 |
|  | 50 | 90 |
| 21 | 500 | 100 |
|  | 50 | 0 |
| 26 | 500 | 100 |
|  | 50 | 10 |
| 27 | 500 | 100 |
|  | 50 | 0 |
| 29 | 500 | 100 |
|  | 50 | 20 |

TABLE 3-continued

| Compound No. | Concn. of Active Ingredient (ppm) | Mortality (%) |
| --- | --- | --- |
| 30 | 500 | 100 |
|  | 50 | 100 |
| 31 | 500 | 100 |
|  | 50 | 50 |
| 32 | 500 | 100 |
|  | 50 | 10 |
| 33 | 500 | 100 |
|  | 50 | 70 |
| 34 | 500 | 100 |
|  | 50 | 100 |
| 35 | 500 | 100 |
|  | 50 | 80 |
| 36 | 500 | 100 |
|  | 50 | 20 |
| 37 | 500 | 100 |
|  | 50 | 90 |
| 38 | 500 | 100 |
|  | 50 | 50 |
| 39 | 500 | 100 |
|  | 50 | 40 |
| 40 | 500 | 100 |
|  | 50 | 0 |
| 41 | 500 | 100 |
|  | 50 | 100 |
| 44 | 500 | 100 |
|  | 50 | 90 |
| 45 | 500 | 100 |
|  | 50 | 90 |
| 46 | 500 | 100 |
|  | 50 | 100 |
| 47 | 500 | 100 |
|  | 50 | 50 |
| 49 | 500 | 100 |
|  | 50 | 0 |
| 50 | 500 | 100 |
|  | 50 | 10 |
| 51 | 500 | 100 |
|  | 50 | 50 |
| 53 | 500 | 100 |
|  | 50 | 10 |
| Comparative Compound A | 500 | 100 |
|  | 50 | 10 |
| Untreated | — | 0 |

The Comparative Compound A as set forth in Table 3 is a compound represented by the following structural formula and disclosed in Japanese Unexamined Patent Publication No. Sho 61-267594:

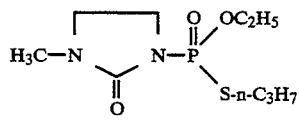

Test Example 2

The emulsifiable concentrate obtained by Formulation Example 2 was diluted with water to 500 ppm and the seedlings of rice plant were immersed therein for 10 seconds. After air-drying, the seedlings whose roots were wrapped round with absorbent cotton were introduced into a test tube, then 10 second instar larvae of green rice leafhopper were put into the test tube, the opening thereof was closed with gauze. The tube was placed in a thermostated room maintained at 26° C. After 2 days, the number of surviving larvae was recorded to obtain the mortality (%) (repeated two times). The results thus obtained are summarized in the following Table 4.

TABLE 4

| Compound No. | Concn. of Active Ingredient (ppm) | Mortality (%) |
| --- | --- | --- |
| 1 | 500 | 100 |
| 3 | 500 | 100 |
| 4 | 500 | 100 |
| 5 | 500 | 100 |
| 9 | 500 | 100 |
| 10 | 500 | 100 |
| 11 | 500 | 100 |
| 14 | 500 | 100 |
| 15 | 500 | 100 |
| 16 | 500 | 100 |
| 17 | 500 | 100 |
| 18 | 500 | 100 |
| 19 | 500 | 100 |
| 20 | 500 | 100 |
| 21 | 500 | 100 |
| 26 | 500 | 100 |
| 27 | 500 | 100 |
| 28 | 500 | 100 |
| 29 | 500 | 100 |
| 30 | 500 | 100 |
| 31 | 500 | 100 |
| 32 | 500 | 100 |
| 33 | 500 | 100 |
| 34 | 500 | 100 |
| 35 | 500 | 100 |
| 37 | 500 | 100 |
| 38 | 500 | 100 |
| 40 | 500 | 100 |
| 41 | 500 | 100 |
| 44 | 500 | 100 |
| 45 | 500 | 100 |
| 46 | 500 | 100 |
| 47 | 500 | 100 |
| 49 | 500 | 100 |
| 50 | 500 | 100 |
| 51 | 500 | 100 |
| 53 | 500 | 100 |
| Comparative Compound A | 500 | 100 |
| Untreated | — | 0 |

The comparative Compound A as set forth in Table 4 is the same as that defined above in connection with Table 3.

Test Example 3

A kidney bean leaf was cut into 3×5 cm². The leaf was put on a filter paper wetted with water for preventing drying of the leaf and female adults of kanzawa spider mite were released on the leaf. After 24 hours, 500 ppm and 50 ppm of concentration of active ingredient prepared by diluting with water the emulsifiable concentrate obtained by Formulation Example 2 were sprayed on the leaf. After air-drying, the mites were held in a thermostated room maintained at 26° C. After 24 hours, the number of surviving adults were recorded to obtain the mortality (%) (repeated two times). The results thus obtained are summarized in the following Table 5.

TABLE 5

| Compound No. | Concn. of Active Ingredient (ppm) | Mortality (%) |
| --- | --- | --- |
| 1 | 500 | 100 |
|  | 50 | 0 |
| 2 | 500 | 100 |
|  | 50 | 0 |
| 3 | 500 | 100 |
|  | 50 | 80 |
| 4 | 500 | 100 |
|  | 50 | 20 |
| 5 | 500 | 100 |
|  | 50 | 40 |

TABLE 5-continued

| Compound No. | Concn. of Active Ingredient (ppm) | Mortality (%) |
|---|---|---|
| 6 | 500 | 100 |
|   | 50 | 50 |
| 7 | 500 | 100 |
|   | 50 | 90 |
| 9 | 500 | 100 |
|   | 50 | 60 |
| 10 | 500 | 100 |
|    | 50 | 70 |
| 11 | 500 | 100 |
|    | 50 | 80 |
| 12 | 500 | 100 |
|    | 50 | 0 |
| 14 | 500 | 100 |
|    | 50 | 80 |
| 15 | 500 | 100 |
|    | 50 | 10 |
| 16 | 500 | 100 |
|    | 50 | 0 |
| 17 | 500 | 100 |
|    | 50 | 30 |
| 18 | 500 | 100 |
|    | 50 | 90 |
| 19 | 500 | 100 |
|    | 50 | 0 |
| 20 | 500 | 100 |
|    | 50 | 0 |
| 26 | 500 | 100 |
|    | 50 | 30 |
| 27 | 500 | 100 |
|    | 50 | 20 |
| 28 | 500 | 100 |
|    | 50 | 30 |
| 29 | 500 | 100 |
|    | 50 | 50 |
| 30 | 500 | 100 |
|    | 50 | 20 |
| 31 | 500 | 100 |
|    | 50 | 10 |
| 32 | 500 | 100 |
|    | 50 | 0 |
| 33 | 500 | 100 |
|    | 50 | 0 |
| 34 | 500 | 100 |
|    | 50 | 20 |
| 35 | 500 | 100 |
|    | 50 | 10 |
| 36 | 500 | 100 |
|    | 50 | 10 |
| 37 | 500 | 100 |
|    | 50 | 50 |
| 38 | 500 | 100 |
|    | 50 | 20 |
| 39 | 500 | 100 |
|    | 50 | 0 |
| 40 | 500 | 100 |
|    | 50 | 10 |
| 41 | 500 | 100 |
|    | 50 | 80 |
| 44 | 500 | 100 |
|    | 50 | 10 |
| 45 | 500 | 100 |
|    | 50 | 10 |
| 46 | 500 | 100 |
|    | 50 | 20 |
| 47 | 500 | 100 |
|    | 50 | 20 |
| 50 | 500 | 100 |
|    | 50 | 0 |
| 51 | 500 | 100 |
|    | 50 | 10 |
| 53 | 500 | 100 |
|    | 50 | 0 |
| Comparative Compound A | 500 | 100 |
|    | 50 | 10 |
| Untreated | — | 0 |

The Comparative Compound A is the same as that defined above in connection with Table 3.

Test Example 4

To a 1/5,000 are pot, soil contaminated with root-knot nematodes was packed and the soil was admixed with the granules obtained by Formulation Example 3 in an amount of 250 g and 25 g/are expressed in terms of the amount of the active ingredient. Two days after the treatment, seedlings of tomato at 3rd to 4th-leaf stage were transplanted in the soil. Twenty-five days after the transplantation, the degree of the invasion of root-knot nematodes (root-knot index) was determined (repeated two times).

The root-knot index was evaluated on the basis of the following evaluation criteria:

| | |
|---|---|
| 0 | no invasion of root-knot nematodes |
| 1 | slight invasion of root-knot nematodes |
| 2 | medium invasion of root-knot nematodes |
| 3 | severe invasion of root-knot nematodes |
| 4 | very severe invasion of root-knot nematodes |

The results thus obtained are summarized in the following Table 6.

TABLE 6

| Compound No. | Amount of Active Ingredient (g/are) | Root-Knot Index |
|---|---|---|
| 1 | 250 | 0 |
|   | 25 | 3 |
| 2 | 250 | 0 |
|   | 25 | 2 |
| 3 | 250 | 0 |
|   | 25 | 0 |
| 4 | 250 | 0 |
|   | 25 | 0 |
| 5 | 250 | 0 |
|   | 25 | 1 |
| 6 | 250 | 0 |
|   | 25 | 3 |
| 7 | 250 | 0 |
|   | 25 | 1 |
| 8 | 250 | 0 |
|   | 25 | 2 |
| 9 | 250 | 0 |
|   | 25 | 0 |
| 10 | 250 | 0 |
|    | 25 | 2 |
| 12 | 250 | 0 |
|    | 25 | 3 |
| 14 | 250 | 0 |
|    | 25 | 0 |
| 15 | 250 | 0 |
|    | 25 | 0 |
| 16 | 250 | 0 |
|    | 25 | 1 |
| 17 | 250 | 0 |
|    | 25 | 0 |
| 18 | 250 | 0 |
|    | 25 | 0 |
| 20 | 250 | 0 |
|    | 25 | 0 |
| 21 | 250 | 0 |
|    | 25 | 3 |
| 25 | 250 | 0 |
|    | 25 | 3 |
| 26 | 250 | 0 |
|    | 25 | 0 |
| 27 | 250 | 0 |
|    | 25 | 0 |
| 29 | 250 | 0 |
|    | 25 | 0 |
| 30 | 250 | 0 |
|    | 25 | 0 |
| 31 | 250 | 0 |
|    | 25 | 0 |
| 33 | 250 | 0 |
|    | 25 | 2 |
| 34 | 250 | 0 |

TABLE 6-continued

| Compound No. | Amount of Active Ingredient (g/are) | Root-Knot Index |
|---|---|---|
|  | 25 | 0 |
| 35 | 250 | 0 |
|  | 25 | 0 |
| 36 | 250 | 0 |
|  | 25 | 2 |
| 37 | 250 | 0 |
|  | 25 | 0 |
| 38 | 250 | 0 |
|  | 25 | 0 |
| 39 | 250 | 0 |
|  | 25 | 0 |
| 40 | 250 | 0 |
|  | 25 | 0 |
| 41 | 250 | 0 |
|  | 25 | 0 |
| 43 | 250 | 0 |
|  | 25 | 3 |
| 44 | 250 | 0 |
|  | 25 | 0 |
| 45 | 250 | 0 |
|  | 25 | 3 |
| 47 | 250 | 0 |
|  | 25 | 3 |
| 49 | 250 | 0 |
|  | 25 | 2 |
| 50 | 250 | 0 |
|  | 25 | 0 |
| 51 | 250 | 0 |
|  | 25 | 0 |
| 53 | 250 | 0 |
|  | 25 | 0 |
| 54 | 250 | 0 |
|  | 25 | 1 |
| Comparative Compound A | 250 | 0 |
|  | 25 | 2 |
| Comparative Compound B | 250 | 0 |
|  | 25 | 1 |
| Untreated | — | 4 |

The Comparative Compound A as set forth in Table 6 is the same as that defined above in connection with Table 3 and Comparative Compound B is a compound (oxamyl) represented by the following structural formula:

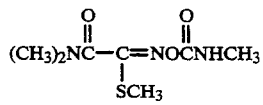

EFFECT OF THE INVENTION

The compounds of the present invention represented by the foregoing general formula (I) exhibit effectiveness in controlling harmful insects, mites and nematodes and thus can be used as novel insecticides, acaricides and nematocides which do not give off a bad or irritating odor and have low toxicity to warm-blooded animals.

We claim:

1. An organophosphorus compound represented by formula (I):

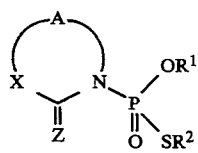

wherein $R^1$ and $R^2$ each represents a $C_{1-4}$ alkyl;

X represents O, S, $CH_2$, (wherein $R^3$ represents a $C_{1-3}$ alkyl), NH or N—$R^4$ (wherein $R^4$ represents $C_{1-4}$ alkyl substituted with at least one group selected from the group consisting of alkoxy, alkylthio, cyano, alkoxyalkyloxy, alkylamino and halogen; alkenyl; halogen substituted alkenyl; alkynyl; halogen substituted alkynyl; phosphoric acid ester; cyano; a group of formula II:

(wherein $R^5$ represents alkyl, halogen substituted alkyl, alkylamino or halogen substituted alkylamino); or —$(R^6)_n$—CO—$R^7$ (wherein n is 0 or 1; $R^6$ represents methylene, alkyl substituted methylene, ethylene and alkyl substituted ethylene; and $R^7$ represents alkyl, halogen substituted alkyl, alkoxy, halogen substituted alkoxy, alkylthio, alkylamino or hydrogen);

Z represents N-$R^8$ (wherein $R^8$ represents nitro, cyano, alkylsulfonyl, halogen substituted alkylsulfonyl, tosyl, alkylcarbonyl, halogen substituted alkylcarbonyl); or C(CN)$R^9$ (wherein $R^9$ represents cyano or alkoxycarbonyl); and A represents an ethylene, $C_{1-3}$ alkyl substituted ethylene, trimethylene, $C_{1-3}$ alkyl substituted trimethylene or —$CH_2NR^{10}CH_2$— (wherein $R^{10}$ is $C_{1-3}$ alkyl), wherein when X is NH or N—$R^4$, A is trimethylene, $C_{1-3}$ alkyl substituted trimethylene or —$CH_2NR^{10}CH_2$— (wherein $R^{10}$ is $C_{1-3}$ alkyl), excluding an organophosphorus compound of formula (I) in which $R^1$ and $R^2$ are $C_{1-4}$ alkyl, X is NH, Z is cyanoimino or nitroimino, and A is trimethylene or $C_{1-3}$ alkyl substituted trimethylene.

2. An organophosphorus compound which is O-ethyl-S-sec-butyl-(3-methyl-2-cyanoimino-1-tetrahydropyrimidinyl)phosphonothiolate.

3. The organophosphorus compound according to claim 1 which is O-ethyl-S-sec-butyl-1-pyrrolidinylphosphonothiolate.

4. An insecticidal, acaricidal or nematocidal composition comprising a carrier and as an active ingredient, an organophosphorus compound represented by formula (I):

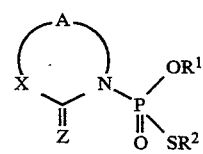

wherein $R^1$ and $R^2$ each represents a $C_{1-4}$ alkyl;

X represents O, S, $CH_2$, CH—$R^3$ (wherein $R^3$ represents a $C_{1-3}$ alkyl), NH or N—$R^4$ (wherein $R^4$ represents $C_{1-4}$ alkyl substituted with at least one group selected from the group consisting of alkoxy, alkylthio, cyano, alkoxyalkyloxy, alkylamino and halogen; alkenyl; halogen substituted alkenyl; alkynyl; halogen substituted alkynyl; phosphoric acid ester; cyano; a group of formula II:

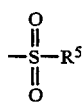 (II)

(wherein $R^5$ represents alkyl, halogen substituted alkyl, alkylamino or halogen substituted alkylamino); or —$(R^6)_n$—CO—$R^7$ (wherein n is 0 or 1; $R^6$ represents methylene, alkyl substituted methylene, ethylene and alkyl substituted ethylene; and $R^7$ represents alkyl, halogen substituted alkyl, alkoxy, halogen substituted alkoxy, alkylthio, alkylamino or hydrogen );

Z represents N—$R^8$ (wherein $R^8$ represents nitro, cyano, alkylsulfonyl, halogen substituted alkylsulfonyl, tosyl, alkylcarbonyl, halogen substituted alkylcarbonyl); or C(CN)$R^9$ (wherein $R^9$ represents cyano or alkoxycarbonyl); and A represents an ethylene, $C_{1-3}$ alkyl substituted ethylene, trimethylene, $C_{1-3}$ alkyl substituted trimethylene or —$CH_2NR^{10}CH_2$— (wherein $R^{10}$ is $C_{1-3}$ alkyl), wherein when X is NH or N—$R^4$, A is trimethylene, $C_{1-3}$ alkyl substituted trimethylene or —$CH_2NR^{10}CH_2$— (wherein $R^{10}$ is $C_{1-3}$ alkyl), excluding an organophosphorus compound of formula (I) in which $R^1$ and $R^2$ are $C_{1-4}$ alkyl, X is NH, Z is cyanoimino or nitroimino, and A is trimethylene or $C_{1-3}$ alkyl substituted trimethylene.

5. An insecticidal, acaricidal or nematocidal composition according to claim 4 wherein the active ingredient compound is O-ethyl-S-sec-butyl-1-pyrrolidinyl-phosphonothiolate.

6. An insecticidal, acaricidal or nematocidal composition comprising a carrier and as an active ingredient compound O-ethyl-S-sec-butyl-(3-methyl-2-cyanoimino-1-tetrahydropyrimidinyl)phosphonothiolate.

* * * * *